United States Patent [19]

Schwuger et al.

[11] 4,071,377
[45] Jan. 31, 1978

[54] METHOD OF MECHANICAL DISHWASHING AND COMPOSITIONS

[75] Inventors: Milan Johann Schwuger, Haan; Heinz Smolka, Langenfeld; Theodor Altenschopfer; Manfred Rostek, both of Dusseldorf, all of Germany

[73] Assignee: Henkel Kommanditgesellschaft auf Aktien (Henkel KGaA), Dusseldorf-Holthausen, Germany

[21] Appl. No.: 458,333

[22] Filed: Apr. 5, 1974

[30] Foreign Application Priority Data

May 7, 1973 Austria .................................. 4012/73
June 29, 1973 Austria .................................. 5757/73
Aug. 16, 1973 Austria .................................. 7160/73
Nov. 9, 1973 Austria .................................. 9450/73

[51] Int. Cl.² ............... A47L 15/00; C02B 1/44; C11D 3/12; C11D 3/60
[52] U.S. Cl. ................... 134/29; 252/89 R; 252/99; 252/131; 252/140; 252/179; 423/329
[58] Field of Search ........... 252/89, 131, 135, 140, 252/179, 99; 423/329; 134/26, 29

[56] References Cited

U.S. PATENT DOCUMENTS

| | | | |
|---|---|---|---|
| 1,642,880 | 9/1927 | Kriegsheim | 423/329 |
| 2,677,665 | 5/1954 | James | 252/131 |
| 2,739,073 | 3/1956 | Bertorelli | 106/288 |
| 2,882,243 | 4/1959 | Milton | 423/329 X |
| 3,112,176 | 11/1963 | Haden | 423/329 |
| 3,154,494 | 10/1964 | Speak | 252/96 |
| 3,700,599 | 10/1972 | Mizuno | 252/99 |
| 3,755,180 | 8/1973 | Austin | 252/99 |

FOREIGN PATENT DOCUMENTS

| | | | |
|---|---|---|---|
| 2,055,423 | 5/1972 | Germany | 252/179 |
| 2,422,655 | 11/1974 | Germany | 252/131 |
| 2,433,485 | 2/1975 | Germany | 252/131 |
| 2,143,771 | 3/1972 | Germany | 252/99 |
| 1,333,810 | 10/1973 | United Kingdom | 252/99 |

OTHER PUBLICATIONS

W. Appelius: "Water Softening by the Permutite Method," Chem. Abstracts, vol. 4, p. 630.
J. D. Glasgow: "The Use of Permutit and Polarit in Water Purification," Chem. Abstracts, vol. 9, p. 676.

*Primary Examiner*—Dennis L. Albrecht
*Attorney, Agent, or Firm*—Hammond & Littell

[57] ABSTRACT

A method for the mechanical washing of dishes, wherein the soiled dishes are treated with an aqueous alkaline liquor having a pH of from 8 to 13 which contains at least one compound inhibiting alkaline earth metal ion precipitation, rinsing and recovering cleaned dishes comprising using finely-dispersed, water-insoluble silicate compounds having a calcium-binding power of at least 50 mg CaO/gm of anhydrous substance and having the formula, combined water not shown, of

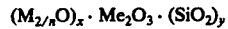

$(M_{2/n}O)_x \cdot Me_2O_3 \cdot (SiO_2)_y$ where M is a cation of the valence $n$, exchangeable with calcium, $x$ is a number of from 0.7 to 1.5, Me is a member selected from aluminum and boron and $y$ is a number of from 0.8 to 6, as said compound inhibiting alkaline earth metal ion precipitation as well as alkaline-reacting mechanical dish washing compositions containing said silicate compounds.

1 Claim, No Drawings

METHOD OF MECHANICAL DISHWASHING AND COMPOSITIONS

THE PRIOR ART

As known, the dishwashing agents used in the household, in commercial enterprises and in industry frequently contain large amounts of condensed phosphates, particularly sodium tripolyphosphate, which are to a great extent responsible for the good cleaning action of these detergents. The phosphorus content of these agents have been criticized by the public in connection with questions of the protection of the environment. The view is frequently expressed that the phosphates, which arrive in the rivers and lakes after treatment of the sewage, have great influence on the eutrophication of the waters, and is said to lead to an increase of the growth of algae and of oxygen consumption. It has, therefore, been tried to eliminate phosphate from the washing and cleaning purposes or from the agents used for this purpose, or at least to substantially reduce its proportion.

In copending, commonly-assigned U.S. pat. application Ser. No. 458,306 filed Apr. 5, 1974, now abandoned, and its continuation application Ser. No. 800,308, filed May 25, 1977, an improvement in the process of washing and bleaching textiles, is described wherein the soiled solid textiles are contacted with an aqueous solution containing a water softening agent for a time sufficient to disperse or dissolve the soil from said soiled articles into said aqueous solution, separating said aqueous solution and recovering said articles substantially soil-free. This improvement consists of using at least one finely-dispersed water-insoluble silicate compound containing at least some combined water and having a calcium binding power of at least 50 mg CaO/gm of anhydrous active substance and the formula on the anhydrous basis $$(M_{2/n}O)_x \cdot Me_2O_3 \cdot (SiO_2)_y$$

where M is a cation of the valence $n$, exchangeable with calcium, $x$ is a member of from 0.7 to 1.5, Me is a member selected from the group consisting of aluminum and boron, and $y$ is a number from 0.8 to 6, as said water softening agent.

The calcium binding power of the silicate compounds can be as high as 200 mg CaO/gm of anhydrous active substance (AS) and preferably is in the range of 100 to 200 mg CaO/gm AS.

The cation M employed is preferably sodium. However, the same can also be totally or partially replaced by other cations exchangeable with calcium, such as hydrogen, lithium, potassium, ammonium or magnesium, as well as by the cations of water-soluble organic bases, for example, by those of primary, secondary or tertiary alkylamines or alkylolamines with not more than 2 carbon atoms per alkyl radical, or not more than 3 carbon atoms per alkylol radical.

OBJECTS OF THE INVENTION

An object of the present invention is the solution of the above-outlined problem of finding a non-polluting mechanical dishwashing method which does not have the above-described inconveniences and which particularly does not burden the waste water with phosphate.

Another object of the present invention is the development in the process of mechanically washing of soiled dishes by mechanically contacting soiled dishes with an alkaline aqueous solution at a pH of from 8 to 13 containing a sufficient amount of a water softening agent whereby the soil on said soiled dishes is dispersed or dissolved, rinsing said dishes with a clear rinse liquid and recovering said dishes substantially soil-free, the improvement which consists of using at least one finely-dispersed, water-insoluble silicate compound containing at least some combined water and having a calcium binding power of at least 50 mg CaO/gm of anhydrous active substance and the formula on the anhydrous basis $$(M_{2/n}O)_x \cdot Me_2O_3 \cdot (SiO_2)_y$$

where M is a cation of the valence $n$, exchangeable with calcium, $x$ is a number of from 0.7 to 1.5, Me is a member selected from the group consisting of aluminum and boron, and $y$ is a number from 0.8 to 6, as said water softening agent.

A yet further object of the present invention is the development of a dishwashing composition for mechanically washing soiled dishes comprising the above water-insoluble silicate compound and an alkaline pH regulator.

These and other objects of the invention will become more apparent as the description thereof proceeds.

DESCRIPTION OF THE INVENTION

The present invention therefore is a method for the mechanical washing of dishes, wherein the soiled dishes are treated with an aqueous alkaline liquor having a pH of from 8 to 13 which contains at least one compound inhibiting alkaline earth metal ion precipitation, rinsing and recovering cleaned dishes comprising using finely-dispersed, water-insoluble silicate compounds having a calcium-binding power of at least 50 mg CaO/gm of anhydrous active substance and having the formula, combined water not shown, of $$(M_{2/n}O)_x \cdot Me_2O_3 \cdot (SiO_2)_y$$

where M is a cation of the valence $n$, exchangeable with calcium, $x$ is a member of from 0.7 to 1.5, Me is a member selected from aluminum and boron and $y$ is a number of from 0.8 to 6, as said compound inhibiting alkaline earth metal ion precipitation, as well as alkaline-reacting mechanical dish washing compositions containing said silicate compounds.

These compounds will hereafter be called "aluminosilicates" for simplicity's sake. Preferred are sodium aluminosilicates. All data given for their production and use also apply to the other compounds claimed.

The above-defined aluminosilicates can be produced synthetically in a simple manner, for example, by reacting water-soluble silicates with water-soluble aluminates in the presence of water. To this end aqueous solutions of the starting materials can be mixed with each other, or one component which is present in solid form can be reacted with another component which is present as an aqueous solution. The desired aluminosilicates can also be obtained by mixing both solid components in the presence of water. Aluminosilicates can also be produced from $Al(OH)_3$, $Al_2O_3$ or $SiO_2$ by reaction with alkali metal silicate or alkali metal aluminate solutions respectively. Finally, such substances are also formed from the melt, but this method seems of less economical interest because of the required high melting temperature and the necessity of transforming the melt into finely-dispersed products.

The cation-exchanging aluminosilicates to be used according to the invention are only formed if special precipitation conditions are maintained, otherwise products are formed which have no, or an inadequate, calcium exchanging power. The calcium exchanging power of at least 50 mg CaO/gm of anhydrous active substance (AS) is critical to the present process. If aluminosilicates are employed with below the critical limit of calcium exchanging power, very little if any soil removal from the soiled dishes is effected in the absence of other types of calcium sequestering or precipitating agents. The production of useable aluminosilicates according to the invention is described in the experimental part.

The aluminosilicates in aqueous suspension produced by precipitation or by transformation in finely-dispersed form according to other methods can be transformed from the amorphous into the aged or into the crystalline state by heating the suspension to temperatures of 50° to 200° C. However, there is hardly any difference between these two forms as far as the calcium binding power is concerned. Aside from the drying conditions, the calcium binding power of the aluminosilicates is proportional to the amount of aluminum contained therein with reference to the amount of silicon. Nevertheless, the crystalline aluminum silicates are preferred for the purpose of the invention. The preferred calcium binding power, which is in the range of 100 to 200 mg CaO/gm AS, is found primarily in compounds of the composition:

0.7 to 1.1 $Na_2O \cdot Al_2O_3 \cdot 1.3$ to 3.3 $SiO_2$

This summation formula comprises two types of different crystal structures (or their non-crystalline initial products) which also differ by their summation formulas. These are:

0.7 to 1.1 $Na_2O \cdot Al_2O_3 \cdot 1.3$ to 2.4 $SiO_2$     (a)

0.7 to 1.1 $Na_2O \cdot Al_2O_3 \cdot > 2.4$ to 3.3 $SiO_2$     (b)

The different crystal structures can be seen in the X-ray diffraction diagram. The d-values found are given in the examples in the description of the production of the aluminosilicates I and II.

The amorphous or crystalline aluminosilicate contained in the aqueous suspension can be separated by filtration from the remaining aqueous solution and be dried at temperatures of 50° to 800° C, for example. Depending on the drying conditions, the product contains more or less combined water. Anhydrous products are obtained by drying at 800° C. If we want to remove the water completely, this can be done by heating for 1 hour to 800° C. This is the way the AS contents of the aluminosilicates are also determined.

Such high drying temperatures are not recommended for the aluminosilicates to be used according to the invention, preferably the temperature should not exceed 400° C. It is of particular advantage that even products dried at substantially lower temperatures of 80° to 200° C, for example, until the adhering liquid water is removed, can be used for the purposes of the invention. The aluminosilicates thus produced, which contain varying amounts of combined water, are obtained after the disintegration of the dried filter cake, as fine powders whose primary particle size does not exceed 0.1 mm, but is mostly lower and ranges down to dust fineness, for example, to 0.1 $\mu$. It must be kept in mind that the primary particles can be agglomerated to larger structures. In some production methods primary particle sizes ranging from 50 to 1 $\mu$ are obtained.

Of particular advantage are aluminosilicates having at least 80% by weight of particles of 10 to 0.01 $\mu$, preferably 8 to 0.1 L $\mu$. These aluminosilicates preferably contain no primary or secondary particles above 40 $\mu$. As far as the products are crystalline, they are "microcrystalline."

The formation of smaller particle sizes can already be enhanced by the precipitation conditions. For these smaller particle sizes, the intermixed aluminate and silicate solutions, which can also be introduced simultaneously into the reaction vessel, are subjected to great shearing forces. If crystalline aluminosilicates are produced, which are preferred according to the invention, the formation of larger or inter-penetrating crystals is prevented by slowly stirring the crystallizing mass.

Nevertheless, undesired agglomeration of crystal particles can occur during the drying, so that it is advisable to remove these secondary particles in a suitable manner, for example, by air sifting. Aluminosilicates obtained in coarser form, which are ground to the desired particle size, can also be used. Suitable for this purpose are, for example, mills and/or air sifters or combinations thereof. The latter are described, for example, in Ullmann, "Enzylkopadie der technischen Chemie" vol. 1, 1951, p. 632 to 634.

From the sodium aluminosilicates, aluminosilicates of other cations, for example, those of potassium, magnesium or water-soluble organic bases can be produced in a simple manner by the exchange of bases. The use of these compounds instead of the sodium aluminosilicates may be of advantage if a special effect is to be achieved by the supply of the said cations, for example, if the state of dissolution of different surface-active compounds simultaneously present in the composition is to be influenced.

These prepared aluminosilicates, that is, produced prior to their use, are used for the purposes of invention.

The amount of aluminosilicate required to achieve a good washing or cleaning effect depends, on the one hand, on its calcium binding power, and on the other hand, on the amount and the type of soil of the dishes to be mechanically washed, the pH of the aqueous washing liquor, and on the amount and hardness of the water used.

<u>By "dishes" in the sense of the invention, all utensils of ceramic material, glass, plastic, wood or metal which are used in the household,</u> in commercial enterprises and in the industry for storing, preparing and serving foods and drinks and which must be cleaned after use are to be considered. The method according to the invention can thus also be used for the mechanical washing and cleaning, particularly of bottles not only in households, restaurants and hotels, but also in canteens, dairies, in the beverage industry, for example, in breweries, in plants producing or processing soft drinks, mineral water or fruit juices.

But the method is also suitable for washing instruments which have been soiled by residues other than food residues, for example, for washing laboratory instruments.

The aluminosilicates are preferably used in a concentration of 0.5 to 3 gm/l. They are combined particularly with alkaline-reacting substances, which are used in such an amount that the pH-value of the washing liquor is in the range of 8 to 13. Such alkaline-reacting substances are preferably alkali metal silicates and alkali metal carbonates, and, if higher pH values are desired, alkali metal hydroxides.

The effect of the method according to the invention and of the agents for carrying out this method, can be improved by adding small amounts of surface-active compounds particularly non-ionic surface-active compounds. In addition, an addition of oxidizing compounds or substances, particularly activated chlorine compounds, if necessary also percompound, has been found to be of advantage.

The composition of dishwashing agents according to the invention is generally within the following formula: 10% to 60% by weight of alkali metal silicates and/or alkali metal carbonates and/or alkali metal hydroxides, which can be replaced partly by inorganic phosphorus-containing sequestering agents, the latter, if utilized, is in amounts corresponding to the maximum content of phosphorus indicated below, 10% to 65% by weight of aluminosilicates (on the anhydrous basis)

0 to 40% by weight of other common constituents of mechanical dishwasher cleaning compositions.

More particularly, the invention relates to a composition for use in the mechanical washing of dishes consisting essentially of A) from 10% to 60% by weight of a mixture of alkaline reacting compounds consisting of 1) from 25% to 100% by weight of said mixture of alkali metal salts selected from the group consisting of alkali metal silicates, alkali metal carbonates, alkali metal hydroxides and mixtures thereof, and 2) from 0 to 25% by weight of said mixture of inorganic phosphorus-containing compounds capable of sequestering alkaline earth metals, with the proviso that said inorganic phosphorus-containing compounds do not exceed 6% by weight of the overall composition, B) from 10% to 65% by weight on the anhydrous basis of at least one finely-dispersed water-insoluble silicate compound containing at least some combined water and having a calcium binding power of at least 50 mg CaO/gm of anhydrous active substance and the formula on the anhydrous basis $$(M_{2/n}O)_x \cdot Me_2O_3 \cdot (SiO_2)_y$$

where M is a cation of the valence $n$, exchangeable with calcium, $x$ is a member of from 0.7 to 1.5, Me is a member selected from the group consisting of aluminum and boron, and $y$ is a number from 0.8 to 6, and C) from 0% to 60% by weight of other constituents of dishwasher cleaning compositions selected from the group consisting of active chlorine-containing bleaching compounds, active oxygen-containing bleaching compounds, anionic surface-active compounds, non-ionic surface-active compounds, amphoteric surface-active compounds, water-soluble polycarboxylic acid compounds capable of complexing calcium, finely-dispersed, granular, water-insoluble organic cation-exchange resins capable of complexing calcium, inorganic neutral-reacting filler salts and water.

The other common constituents of dishwasher cleaning compositions comprise the following substances which are present mostly in the indicated quantities:

0 to 10% by weight of bleach substances containing activated chlorine or activated oxygen, 0 to 10% by weight of surface-active compounds, particularly non-ionic surface-active compounds, 0 to 20% by weight of sodium sulfate and/or water.

The surface-active compounds or tensides contain in the molecule at least one hydrophobic organic moiety and one water-solubilizing, anionic, non-ionic or amphoteric group. The hydrophobic moiety is mostly an aliphatic hydrocarbon radical with 8 to 26, preferably 10 to 22 and particularly 12 to 18 carbon atoms or an alkyl aromatic radical, such as alkylphenyl, with 6 to 18, preferably 8 to 16 aliphatic carbon atoms.

Among the anionic surface-active compounds are, for example, soaps of natural or synthetic, preferably saturated, fatty acids, optionally, also, soaps of resinic or naphthenic acids. Suitable synthetic anionic tensides are those of the type of the sulfonates, sulfates and synthetic carboxylates.

Suitable anionic tensides of the sulfonate type are alkylbenzene sulfonates ($C_{9-15}$ alkyl) mixtures of alkenesulfonates and hydroxyalkanesulfonates, as well as alkanedisulfonates, as they are obtained, for example, from monoolefins with terminal or non-terminal double bonds by sulfonation with gaseous sulfur trioxide and subsequent alkaline or acid hydrolysis of the sulfonation products. Also suitable are alkanesulfonates which are obtained from alkanes by sulfochlorination or sulfoxidation and subsequent hydrolysis or neutralization or by bisulfite addition to olefins. Other suitable tensides of the sulfonate type are the esters of α-sulfofatty acids, for example, the α-sulfonic acids of hydrogenated methyl or ethyl esters of coconut, palmkernel or tallow fatty acids.

Suitable tensides of the sulfate type are the sulfuric acid monoesters of primary alcohols (e.g. from coconut fatty alcohols, tallow fatty alcohols or oleyl alcohol) and those of secondary alcohols. Also suitable are sulfated fatty acid alkanolamides, sulfated fatty acid monoglycerides or sulfated reaction products of 1 to 4 mols of ethylene oxide with primary or secondary fatty alcohols or alkylphenols.

Other suitable anionic tensides are the fatty acid esters or amides of hydroxy- or amino-carboxylic acids or sulfonic acids, such as the fatty acid sarcosides, fatty acid glycolates, fatty acid lactates, fatty acid taurides or fatty acid isoethionates.

The anionic tensides can be present in the form of their alkali metal salts, such as the sodium or potassium salts, the ammonium salts, as well as soluble salts of organic bases, such as the lower alkylolamines, for example, mono-, di- or triethanol amine.

Suitable non-ionic surface-active compounds or tensides are the addition products of 4 to 40, preferably 4 to 20 mols of ethylene oxide to 1 mol of a fatty alcohol, alkylphenol, fatty acid, fatty amine, fatty acid amine or alkanesulfonamide. Particularly important are the addition products of 5 to 15 mols of ethylene oxide to coconut fatty alcohols or tallow fatty alcohols, to oleyl alcohol or to secondary alkanols with 8 to 18, preferably 12 to 18 carbon atoms, as well as monoalkylphenols or dialkylphenols with 6 to 14 carbon atoms in the alkyls. In addition to these water-soluble non-ionics, polyglycol ethers with 1 to 4 ethylene glycol ether radicals in the molecule, which are insoluble or not completely water-soluble, are also of interest, particularly if they are used together with water-soluble non-ionic or anionic tensides.

Furthermore, the water-soluble addition products of ethylene-oxide to polyoxypropylene glycol containing 10 to 100 propylene glycol ether groups (Pluronics ®), to alkylenediaminepolyoxypropylene glycol (Tetronics ®), and to alkylpolyoxypropylene glycols with 1 to 10 carbon atoms in the alkyl chain, can also be used where the polyoxypropylene glycol chain acts as a hydrophobic radical.

Non-ionic tensides of the type of the amine oxides or sulfoxides can also be used.

Among the compounds serving as bleaching agents and releasing $H_2O_2$ in water, sodium perborate tetrahydrate ($NaBO_2 . H_2O_3 . 3 H_2O$) and the monohydrate ($NaBO_2 . H_2O_2$) are of particular importance. But also other $H_2O_2$ releasing borates can also be used, such as perborax $Na_2B_4O_7 . 4 H_2O$. These compounds can be replaced partly or completely by other carriers of active oxygen, particularly by peroxyhydrates, such as peroxycarbonates, ($Na_2CO_3 . 1.5 H_2O_2$), peroxypyrophosphates, citrate perhydrates, urea-$H_2O_2$ compounds, as well as by $H_2O_2$-releasing peracid salts, such as Caroates ($KHSO_5$), perbenzoates or peroxyphthalates.

The activated chlorine compounds serving as bleaching agents can be of an inorganic or organic nature.

The inorganic active chlorine compounds include alkaline metal hypochlorites, which can be used particularly in the form of their mixed salts or addition compounds with orthophosphates or on condensed phosphates such as with alkali metal pyrophosphates and polyphosphates, or with alkali metal silicates. If the dishwashing agent compositions contain monopersulfates and chlorides, active chlorine is formed in aqueous solution.

The organic active-chlorine compounds which can be used are particularly the N-chloro compounds, where one or two chlorine atoms are linked to a nitrogen atom, the third valence of the nitrogen atoms leading preferably to a negative group, particularly to a CO- or $SO_2$-group. These compounds include dichlorocyanuric acid and trichlorocyanuric acid or their salts, chlorinated alkylguanides or alkylbiguanides, chlorinated hydantoins and chlorinated melamines.

The cleaning action of the aluminosilicates can be improved by water-soluble polycarboxylic acids capable of forming complexes with calcium, or their water-soluble salts. The aluminosilicates can be replaced partly by the above-mentioned additives.

The sequestering agents of the type of the water-soluble polycarboxylic acids to be used according to the invention in combination with the above-defined aluminosilicates, which are preferably used in the form of their water-soluble salts are, for example, the carboxymethyl ethers of sugar, starch and cellulose. They also include the water-soluble polymers of acrylic acid, hydroxyacrylic acid, maleic acid, itaconic acid, mesaconic acid, aconitic acid, methylenemalonic acid, citraconic acid, etc., the copolymers of said carboxylic acids with each other or with ethylenic-unsaturated compounds, like ethylene, propylene, isobutylene, vinyl alcohol, vinylmethyl ether, furan, acrolein, vinyl acetate, acrylamide, acrylonitrile, methacrylic acid, crotonic acid, etc., such as 1:1 copolymers of maleic acid anhydride and ethylene or propylene or furan, play a particular part.

Other polymeric carboxylic acids of the type of polyhydroxypolycarboxylic acids or polyaldehydropolycarboxylic acids are substances substantially composed of acrylic acid and acrolein units or of acrylic acid and vinyl alcohol-units, which can be obtained by copolymerization of acrylic acid and acrolein or by polymerization of acrolein and subsequent Cannizzaro reaction, if necessary, in the presence of formaldehyde.

These polymeric carboxylic acids are preferably those which can be considered according to their structure as homopolymers or copolymers of alkenoic acids or alkenedioic acids, containing not more than 6 carbon atoms in the molecule, or as their copolymers with unsaturated hydrocarbons (alkenes), alcohols (alkenols), ethers (alkenylalkyl ethers), aldehydes (alkenals), esters (vinyl alkanoates), alkenoic acid amides or alkenoic acid nitriles containing not more than 6 carbon atoms in the molecule, even if they are not obtained by the polymerization of a mixture of the corresponding starting materials.

The combinations of aluminosilicates and polymeric carboxylic acids or their salts to be used according to the invention are used preferably in concentrations of 0.5 to 3 gm/l. The ratio of aluminosilicate to polymeric carboxylic acids range from 10:1 to 1:10, preferably from 4:1 to 1:4.

The invention also concerns an embodiment of the above-described method and of the agents necessary for carrying out this method, both of which are characterized in that the above-defined aluminosilicates are replaced partly by finely-dispersed, granular, water-insoluble ion-exchange resins of an organic nature capable of binding calcium. These are synthetic resin ion-exchangers which have preferably a calcium binding power of 20 to 220, particularly 50 to 150 mg CaO/gm of active substance.

The particle size of the organic ion-exchangers can be in the range of the commercial ion-exchangers (0.1 to 1 mm). Preferably products with a particle size of 0.3 to 0.8 mm are used. The commercial products can be readily reduced to the desired particle size, if necessary.

The "granular" ion exchangers are those of cylindrical, spherical or bead form, and those of irregular form, for example, ground products with irregular fractures, but the particle itself should represent a compact mass.

The ion-exchanging groups capable of binding calcium are, for example, sulfonic acid groups, phosphonic acid groups, carboxylic acid groups, carboxymethyl groups, sulfonamide groups, disulfimide groups, carbonamide groups, dicarbimide groups and sulfocarbimide groups. These groups are linked to a cross-linked and therefore water-insoluble skeleton (which may swell in water, if necessary) of a macromolecule, which can be a polycondensation or a polymerization resin, depending on its production.

The polycondensation resins are obtained, for example, by reacting phenols or phenol derivatives containing acid groups with aldehydes or ketones, particularly with formaldehyde. The acid groups can also be introduced after the condensation.

Polymerization resins are obtained by copolymerization of styrene or of styrene drivatives containing acid groups with cross-linking agents, such as divinylbenzene, and subsequent introduction of acid groups, if necessary. The styrene can be replaced by polymerizable carboxylic acids.

These organic cation-exchange resins are use preferably in the form of their salts. The cations capable of exchange with calcium can be the same as in the aluminosilicates.

The combinations of aluminosilicates and organic ion-exchange resins or their salts to be used according to the invention are used preferably in concentrations of 0.5 to 3 gm/l. The ratio of aluminosilicate to organic ion-exchanger is in the range of 10:1 to 1:10, preferably 4:1 to 1:4.

By using the above-described aluminosilicates according to the invention it is readily possible, even when using phosphorus-containing inorganic or organic sequestering or precipitating agents for calcium, to keep the phosphorus content of the dishwasher liquors at a maximum of 0.6 gm/l, preferably at a maximum of 0.3 gm/l, and their content in the compositions to not more than 6% by weight, preferably not more than 3% by weight. But it is also possible to effect the method of the invention in the absence of phosphorus-containing compounds with good results.

The following specific embodiments are illustrative of the invention without being limitative in any respect.

EXAMPLES

First, the production of the finished aluminosilicates is described, for which no invention is claimed.

PROCESS CONDITIONS

The aluminate solution, diluted with deionized water was mixed in a vessel of 15 liter capacity, under vigorous stirring with the silicate solution. Both solutions were at room temperature. An X-ray amorphous sodium aluminosilicate was formed in the exothermic reaction as a primary precipitation product. After stirring for 10 minutes, the suspension of the precipitation product was either separated as an amorphous product or transferred to a crystallization vessel where it remained for some time at the elevated temperature given, to crystallize. After draining off the liquor from the crystals and washing with deionized water until the outflowing wash water had a pH-value of about 10, the filter residue was dried. When there is any deviation from this general production procedure, this is mentioned explicitly in the specific part. Thus, for example, in some cases for the practical tests, the homogenized uncrystallized suspension of the precipitation product or the crystal sludge was used. The water content was determined by heating the product for one hour to 800° C.

In the production of microcrystalline aluminosilicates, indicated by the suffix "$m$", the aluminate solution diluted with deionized water was mixed with the silicate solution and mixed in a high-speed intensive stirrer (10,000 rpm, "Ultraturrax", made by Janke & Kunkel IKA-Werk, Stauffen/Breisgau/Federal Republic of Germany). After vigorous stirring for 10 minutes, the suspension of the amorphous precipitation product was transferred to a crystallization vessel where the formation of large crystals was prevented by stirring the suspension. After draining off the liquor and washing with deionized water until the outflowing water had a pH value of about 10, the filter residue was dried, then ground in a ball mill and separated in a centrifugal sifter ("Microplex" air sifter, made by Alpine, Augsburg, Federal Republic of Germany) into two fractions, of which the finer fraction contained no portions above 10 μ. The particle size distribution was determined by means of a sedimentation scale.

The degree of crystallization of an aluminosilicate can be determined from the intensity of the interference lines of an X-ray diffraction diagram of the respective product, compared to the corresponding diagrams of X-ray amorphous or fully crystallized products.

All data in % are in percent by weight.

The calcium binding power of the aluminosilicates or borosilicates was determined in the following manner, 1 liter of an aqueous solution, containing 0.594 gm of $CaCl_2$ (= 300 mg CaO/l = 30° dH) and adjusted to a pH of 10 with diluted NaOH, was mixed with 1 gm of the aluminosilicate or borosilicate (on the anhydrous basis, AS). Then the suspension was stirred vigorously for b 15 minutes at a temperature of 22° (±2° C). After filtering off the aluminosilicate, the residual hardness $x$ of the filtrate was determined. From it, the calcium binding power was calculated in mg CaO/gm. As according to the formula: $(30 - x) \cdot 10$. For shorthand purposes this test procedure will be referred to as the Calcium Binding Power Test Method.

If calcium binding power is determined at higher temperature, for example, at 60° C, better values are obtained than at 22° C. This fact distinguishes the aluminosilicates from most of the soluble sequestering agents that have been suggested so far for use in detergents and represents a particular technical progress in their use.

PRODUCTION CONDITIONS FOR ALUMINOSILICATE I:

Precipitation:
  2.985 kg of an aluminate solution of the composition:
    17.7% $Na_2O$, 15.8% $Al_2O_3$, 66.6% $H_2O$
  0.15 kg of sodium hydroxide
  9.420 kg of water
  2.445 kg of a 25.8% sodium silicate solution of the composition 1 $Na_2O$. 6.0 $SiO_2$, prepared freshly from commercial waterglass and easily alkali-soluble silica
Crystallization: 24 hours at 80° C
Drying 24 hours at 100° C
Composition: 0.9 $Na_2O$ .1 $Al_2O_3$ .2.05 $SiO_2$ .4.3 $H_2O$ (=21.6% $H_2O$)
Degree of crystallization: Fully crystalline
Calcium binding power: 150 mg CaO/gm AS.

If the product obtained was dried for 1 hour at 400° C, an aluminum silicate I$a$ was obtained of the composition:

0.9 $Na_2O$ .1 $Al_2O_3$ .2.04 $SiO_2$ .2.0 $H_2O$ (= 11.4% $H_2O$)

which is likewise suitable for the purposes of the invention.

PRODUCT CONDITIONS FOR ALUMINOSILICATE II:

Precipitation:
  2.115 kg of an aluminate solution of the composition:
    17.7% $Na_2O$ 15.8% $Al_2O_3$, 66.5% $H_2O$
  0.585 kg of sodium hydroxide
  9.615 kg of water
  2.685 kg of a 25.8% sodium silicate solution of the composition: 1 $Na_2O$. 6 $SiO_2$ (prepared as under I)
Crystallization: 24 hours at 80° C
Drying: 24 hours at 100° C and 20 torr.
Composition: 0.8 $Na_2O$. 1 $Al_2O_3$. 2.655 $SiO_2$. 5.2 $H_2O$
Degree of crystallization: Fully crystalline
Calcium binding power: 120 mg CaO/gm AS.

This product too can be dehydrated by drying (for 1 hour at 400° C) to the composition:

0.8 $Na_2O$.1 $Al_2O_3$ .2.65 $SiO_2$ .0.2 $H_2O$

This dehydration product II$a$ is likewise suitable for the purposes of the invention.

The aluminosilicates I and II show in the x-ray diffraction diagram the following interference lines.

| d-values, recorded with Cu-K$_a$-radiation in A | |
| --- | --- |
| I | II |
| — | 14.4 |
| 12.4 | — |
| — | 8.8 |
| 8.6 | — |
| 7.0 | — |
| — | 4.4 (+) |
| 4.1 (+) | — |
| — | 3.8 (+) |
| 3.68 (+) | — |
| 3.38 (+) | — |
| 3.26 (+) | — |
| 2.96 (+) | — |
| — | 2.88 (+) |
| — | 2.79 (+) |
| 2.73 (+) | — |
| — | 2.66 (+) |
| 2.60 (+) | — |

It is quite possible that not all these interference lines will appear in the X-ray diffraction diagram, particularly if the aluminosilicates are not fully crystallized. For this reason, the d-values which are the most important for the characterization of these types are identified by a "(+)".

PRODUCTION CONDITIONS FOR ALUMINOSILICATE III:

Precipitation:
  2.985 kg of an aluminate solution of the composition:
    17.7% Na$_2$O, 15.8% Al$_2$O$_3$, 66.5% H$_2$O
  0.150 kg of sodium hydroxide
  9.420 kg of water
  2.445 kg of a 25.8% sodium silicate solution of the composition: 1 Na$_2$O · 6 SiO$_2$ (prepared as in I)
Crystallization: none, amphorous precipitate
Drying: 24 hours at 25° C and 20 torr.
Composition: 0.9 Na$_2$O .1 Al$_2$O$_3$ .2.04 SiO$_2$ .47 H$_2$O
Degree of crystallization: X-ray amorphous
Calcium binding power: 160 mg CaO/gm AS.

PRODUCTION CONDITIONS FOR ALUMINOSILICATE IV

Precipitation:
  2.985 kg of an aluminate solution of the composition:
    17.7% Na$_2$O, 15.8% Al$_2$O$_3$, 66.5% H$_2$O
  0.150 kg of sodium hydroxide
  9.420 kg of water
  2.445 kg of a 25.8% sodium silicate solution of the composition: 1 Na$_2$O .6 SiO$_2$ (prepared as in I)
Crystallization: None, amorphous precipitate
Drying: 24 hours at 100° C, then 1 hour at 400° C
Composition: 0.9 Na$_2$O .1 Al$_2$O$_3$ .2.04 SiO$_2$ .0.1 H$_2$O
Degree of crystallization: X-ray amorphous
Calcium binding power: Due to the extensive drying of the amorphous precipitate, the calcium binding power was reduced to 20 mg CaO/gm AS: the product was practically unsuitable for the purposes of the invention.

PRODUCTION CONDITIONS FOR ALUMINOSILICATE V:

Precipitation: 4.17 kg of solid aluminate of the composition:
  38% Na$_2$O, 62% Al$_2$O$_3$
  10.83 kg of a 34.9% sodium silicate solution of the composition: 1 Na$_2$O .3.46 SiO$_2$
Crystallization: None, amorphous precipitate
Drying: 24 hours at 100° C
Composition: 1.5 Na$_2$O .1 Al$_2$O$_3$ .2 SiO$_2$ .3 H$_2$O
Degree of crystallization: X-ray amorphous
Calcium binding power: 140 mg CaO/gm AS

PRODUCTION CONDITIONS FOR ALUMINOSILICATE VI:

Precipitation:
  8.37 kg of an aluminate solution of the composition:
    20.0% Na$_2$O, 10.2% Al$_2$O$_3$, 69.8% H$_2$O
  0.09 kg of sodium hydroxide
  5.34 kg of water
  1.20 kg of microcrystalline silica (Aerosil)
Crystallization: None, amorphous precipitate
Drying: 24 hours at 100° C
Composition: 0.9 Na$_2$O .1 Al$_2$O$_3$ .2.04 SiO$_2$ .6.7 H$_2$O
Degree of crystallization: X-ray amorphous
Calcium binding power: 145 mg CaO/gm AS

PRODUCTION CONDITIONS FOR ALUMINOSILICATE VII:

Precipitation:
  3.255 kg of an aluminate solution of the composition:
    17.7% Na$_2$O, 15.8% Al$_2$O$_3$, 66.5% H$_2$O
  0.06 kg of sodium hydroxide
  9.465 kg of water
  2.22 kg of a 34.9% sodium silicate solution of the composition: 1 Na$_2$O · 3.46 SiO$_2$
Crystallization: None, amorphous precipitate
Drying: 24 hours at 100° C
Composition: 1 Na$_2$O .1 Al$_2$O$_3$ .2 SiO$_2$ .1 H$_2$O (=6% H$_2$O)
Degree of crystallization: X-ray amorphous
Calcium binding power: 150 mg CaO/gm AS

PRODUCTION CONDITIONS FOR ALUMINOSILICATE VIII:

Precipitation:
  2.115 kg of an aluminate solution of the composition:
    17.7% Na$_2$O, 15.8% Al$_2$O$_3$, 66.5% H$_2$O
  0.585 kg of sodium hydroxide
  9.615 kg of water
  2.685 of a 25.8% sodium silicate solution of the composition: 1 Na$_2$O · 6 SiO$_2$
Crystallization: None, amorphous precipitate
Drying: 24 hours at 100° C
Composition: 0.8 Na$_2$O .1 Al$_2$O$_3$ .2.65 SiO$_2$ .4 H$_2$O
Degree of crystallization: X-ray amorphous
Calcium binding power: 60 mg CaO/gm AS

PRODUCTION CONDITIONS FOR ALUMINOSILICATE IX:

Precipitation:
  3.41 kg of an aluminate solution of the composition:
    21.4% Na$_2$O, 15.4% Al$_2$O$_3$, 63.2% H$_2$O
  10.46 kg of water
  1.13 kg of a 34.9% sodium silicate solution of the composition: 1 Na$_2$O · 3.46 SiO$_2$
Crystallization: None, amorphous precipitate
Drying: 24 hours at 100° C
Composition: 1 Na$_2$O .1 Al$_2$O$_3$ .1 SiO$_2$ · 1.4 H$_2$O
Degree of crystallization: X-ray amorphous
Calcium binding power: 120 mg CaO/gm AS

PRODUCTION CONDITIONS FOR ALUMINOSILICATE X:

Precipitation:

2.835 kg of an aluminate solution of the composition:
14.2% $Na_2O$, 17.2% $Al_2O_3$, 68.6% $H_2O$
6.93 kg of water
5.235 kg of a 34.9% sodium silicate solution of the composition: 1 $Na_2O \cdot 3.46\ SiO_2$
Crystallization: None, amorphous precipitate
Drying: 24 hours at 100° C
Composition: 1 $Na_2O$ .1 $Al_2O_3$ .5 $SiO_2$ .2.8 $H_2O$
Degree of crystallization: X-ray amorphous
Calcium binding power: 100 mg CaO/gm AS

PRODUCTION CONDITIONS FOR ALUMINOSILICATE XI:

Precipitation:
2.86 kg of an aluminate solution of the composition:
13.8% $Na_2O$, 16.7% $Al_2O_3$, 69.5% $H_2O$
6.01 kg of water
6.13 kg of a 34.9% sodium silicate solution of the composition: 1 $Na_2O \cdot 3.46\ SiO_2$
Crystallization: None, amorphous precipitate
Drying: 24 hours at 100° C
Composition: About 1 $Na_2O$ .1 $Al_2O_3$ .6 $SiO_2$ .3.2 $H_2O$
Degree of crystallization: X-ray amorphous
Calcium binding power: 60 mg CaO/gm AS

PRODUCTION CONDITIONS FOR ALUMINOSILICATE XII:

Precipitation:
2.01 kg of an aluminate solution of the composition:
20.0% $Na_2O$, 10.2% $Al_2O_3$, 69.8% $H_2O$
1.395 kg of sodium hydroxide
9.045 kg of water
2.19 kg of a 25.8% sodium silicate solution of the composition: 1 $Na_2O \cdot 6\ SiO_2$ (prepared as under I)
Crystallization: 24 hours at 80° C
Drying: 24 hours at 100° C
Composition: 0.9 $Na_2O$ .1 $Al_2O_3$ .2 $SiO_2$ .3 $H_2O$
Degree of crystallization: Fully crystalline
Calcium binding power: 160 mg CaO/gm AS

PRODUCTION CONDITIONS FOR ALUMINOSILICATE XIII:

Precipitation:
2.985 kg of an aluminate solution of the composition:
17.7% $Na_2O$, 15.8% $Al_2O_3$, 66.5% $H_2O$
0.150 kg of sodium hydroxide
9.520 kg of water
2.445 kg of a 25.8% sodium silicate solution of the composition: 1 $Na_2O$ .6 $SiO_2$ (prepared as in I)
Crystallization: 24 hours at 80° C
For the production of a potassium aluminosilicate, the liquor was drained off, the residue washed with water and suspended in an aqueous KCl solution. After heating for 30 minutes to 80–90° C, the product was filtered off and washed.
Drying: 24 hours at 100° C
Composition: 0.28 $Na_2O$ .0.62 $K_2O$ .1 $Al_2O_3$ .2.04 $SiO_2$ .4.3 $H_2O$
Degree of crystallization: Fully crystalline
Calcium binding power: 170 mg CaO/gm AS

PRODUCTION CONDITIONS FOR ALUMINOSILICATE XIV:

Precipitation:
8.450 kg of an aluminate solution of the composition:
11.3% $Na_2O$, 18.7% $Al_2O_3$, 70.0% $H_2O$
6.550 kg of a 34.9% sodium silicate solution of the composition: 1 $Na_2O \cdot 3.46\%\ SiO_2$
Crystallization: None, amorphous precipitate
Drying: None
Composition: 1.5 $Na_2O$ .1 $Al_2O_3$ .2 $SiO_2$ .x $H_2O$
Degree of crystallization: X-ray amorphous
Calcium binding power: 120 mg CaO/gm AS

PRODUCTION CONDITIONS FOR ALUMINOSILICATE XV:

Precipitation: As for aluminosilicate XIV
Crystallization: 24 hours at 80° C
Drying: None
Composition: 1.5 $Na_2O$ .1 $Al_2O_3$ .2 $SiO_2$ .x $H_2O$
Degree of crystallization: Fully crystalline
Calcium binding power: 170 mg CaO/gm AS

PRODUCTION CONDITIONS FOR BOROSILICATE XVI:

Precipitation: 3.20 kg of a borate solution of the composition: 19.7% $Na_2O$, 19.7% $B_2O_3$, 60.6% $H_2O$ 9.55 kg of water 2.55 kg of a 34.5% sodium solution of the composition: 1 $Na_2O$ .3.46 $SiO_2$
Crystallization: 24 hours at 80° C
Drying: 24 hours at 100° C and 20 torr.
Composition: 1.5 $Na_2O$ .1 $B_2O_3$ .2 $SiO_2$ .1.5 $H_2O$
Degree of crystallization: Primarily crystalline
Calcium binding power: 120 mg CaO/gm AS The primary particle sizes of the aluminum or boron silicates I – XVI described here range from 10 to 45 m$\mu$.

PRODUCTION CONDITIONS FOR ALUMINOSILICATE Im:

Precipitation: As in aluminosilicate I
Crystallization: 6 hours at 90° C
Drying: 24 hours at 100° C
Composition: 0.9 $Na_2O$ .1 $Al_2O_3$ .2.05 $SiO_2$ .4.3 $H_2O$ (=21.6% $H_2O$)
Degree of crystallization: Fully crystalline
Calcium binding power: 170 mg CaO/gm AS

PRODUCTION CONDITIONS FOR ALUMINOSILICATE IIm:

Precipitation: As for aluminosilicate II
Crystallization: 12 hours at 90° C
Drying: 24 hours at 100° C and 20 torr.
Composition: 0.8 $Na_2O$ .1 $Al_2O_3$ .2.655 $SiO_2$ .5.2 $H_2O$
Degree of crystallization: Fully crystalline
Calcium binding power: 145 mg CaO/gm AS

PRODUCTION CONDITIONS FOR ALUMINOSILICATE XIIm:

Precipitation: As for aluminosilicate XII
Crystallization: 6 hours at 90° C
Composition: 0.9 $Na_2O \cdot 1\ Al_2O_3 \cdot 2\ SiO_2 \cdot 3\ H_2O$
Degree of crystallization: Fully crystalline
Calcium binding power: 175 mg CaO/gm AS

PRODUCTION CONDITIONS FOR ALUMINOSILICATE XIIIm:

Precipitation: As for aluminosilicate XIII
Crystallization: 6 hours at 90° C
For the production of the potassium-aluminum silicate the liquor was drained off, the residue was washed with water and suspended in an aqueous KCl solution. The product was filtered off after heating for 30 minutes to 80°–90° C and washed.

Drying: 24 hours at 100° C
Composition: 0.28 $Na_2O$ .0.62 $K_2O$ .1 $Al_2O_3$ .2.04 $SiO_2$ .4.3 $H_2O$
Degree of crystallization: Fully crystalline
Calcium binding power: 180 mg CaO/gm AS

PRODUCTION CONDITIONS FOR ALUMINOSILICATE XVm:

Precipitation: As for aluminosilicate XIV
Crystallization: 24 hours at 80° C
Drying: The filter cake was not dried but suspended in water after washing and used in this form for the application tests.
Composition: 0.9 $Na_2O$ .1 $Al_2O_3$ .2 $SiO_2$ .X $H_2O$
Degree of crystallization: Fully crystalline
Calcium binding power: 170 mg CaO/gm AS

PRODUCTION CONDITIONS FOR ALUMINOSILICATE XVIIIm:

Precipitation: As for aluminosilicate XIV
Crystallization: 6 hours at 90° C
Drying: 24 hours at 100° C
Composition: 0.9 $Na_2O$ .1 $Al_2O_3$ .2 $SiO_2$ · 4.4 $H_2O$
Degree of crystallization: Fully crystalline
Calcium binding power: 172 mg CaO/gm AS

PRODUCTION CONDITIONS FOR ALUMINOSILICATE XIXm:

Precipitation:
2.96 kg of an aluminate solution of the composition: 17.7% $Na_2O$, 15.8% $Al_2O_3$, 66% $H_2O$
0.51 kg of sodium hydroxide
8.45 kg of water
3.00 kg of a commercial sodium silicate solution of the composition: 8.0% $Na_2O$, 26.9% $SiO_2$, 65.1% $H_2O$
Crystallization: 12 hours at 90° C
Drying: 12 hours at 100° C
Composition: 0.93 $Na_2O$ . 1 $Al_2O_3$ .2.75 $SiO_2$ .5.5 $H_2O$
Degree of crystallization: Fully crystalline
Calcium binding power: 125 mg CaO/gm AS

PRODUCTION CONDITIONS FOR ALUMINOSILICATE XXM:

Precipitation:
0.76 kg of an aluminate of the composition: 36.0% $Na_2O$, 59.0% $Al_2O_3$, 5.0% $H_2O$
0.94 kg of sodium hydroxide
9.49 kg of water
3.94 kg of a commercial sodium silicate solution of the composition: 8.0% $Na_2O$, 26.9% $Al_2O_3$, 65.1% $H_2O$
Crystallization: 12 hours at 90° C
Drying: 12 hours at 100° C
Composition: 0.9 $Na_2O$ · 1 $Al_2O_3$ .3.1 $SiO_2$ .5 $H_2O$
Degree of crystallization: Fully crystalline
Calcium binding power: 110 mg CaO/gm AS The particle size of the above described microcrystalline products Im – XIIIm and XVIIm – XXm, determined by sedimentation analysis, was in the following range:
> 40 μ = 0%
< 10 μ = 100%
< 8 μ = 50 – 95%
maximum range of the particle size distribution curve at 3 – 6 μ

The particle size distribution of the product XVm was in the following range:

> 40 μ = 0%
< 10 μ = 100%
< 8 μ = 99%
maximum range of the particle size distribution curve at 1 – 3 μ

The following examples describe specific embodiments of the method according to the invention and to the agents for carrying out this method. The recipes according to the state of the art are identified by the letter "v" (reference), whereas those according to the invention are identified by the letters "a", "b", "c", and "d".

The aluminosilicates utilized were produced as given above and had the following composition:
I: 0.9 $Na_2O$ .$Al_2O_3$ .2.05 $SiO_2$ .4.3 $H_2O$ (=21.6% $H_2O$) fully crystalline calcium binding power: 150 mg CaO/gm AS
V: 1.5 $Na_2O$ .$Al_2O_3$ .2 $SiO_2$ .3 $H_2O$ (=14.4% $H_2O$) x-ray amorphous calcium binding power: 140 mg CaO/gm AS
VII: $Na_2O$ .$Al_2O_3$ .2 $SiO_2$ .$H_2O$ (=6% $H_2O$) x-ray amorphous calcium binding power: 150 mg CaO/gm AS In the recipes, the amounts for the aluminosilicates refer to their anhydrous active substance, determined by dehydration for 1 hour at 800° C. The water contained in the aluminosilicates is indicated separately, if necessary, together with additional water contained in the detergent.

"DCIC" is the sodium or potassium salt of dichloroisocyanuric acid.

"Liquid waterglass" is a 35% solution of a sodium silicate of the composition $Na_2O$ .3.35 $SiO_2$.

The "Non-ionic" is an addition product of ethylene oxide to a polyoxypropylene glycol with a molecular weight of 1900, which is commercially available under the trademark "Pluronic L 61"; the portion of the polypropylene glycol ethers being 90% by weight and the portion of the polyethylene glycol ethers being 10% by weight.

EXAMPLE 1

In a commercial household dishwashing machine, glass dishes (a), porcelain plates (b) and cups (c) were washed, where (a) were soiled with incrusted or burnt residues of chopped meat, milk and starch pudding, (b) with dried starch or oatmeal cereal, and (c) with wax pencil or dried tea residues, using the following detergents. The hardness of the tap water was reduced to 3° dH, by a base-exchanger installed in the machine. The washing composition concentration was 3 gm/l.

| Component | % by weight of component in the product | | |
|---|---|---|---|
| | v | a | b |
| $Na_5P_3O_{10}$ | 44.0 | 20.0 | 0.0 |
| Aluminosilicate I | 0.0 | 24.0 | 44.0 |
| $Na_2SiO_3$ | 40.0 | 40.0 | 40.0 |
| $Na_2SO_4$ | 10.0 | 3.0 | 0.0 |
| DCIC | 2.0 | 2.0 | 2.0 |
| Non-ionic | 1.0 | 1.0 | 1.0 |
| Water | 3.0 | 10.0 | 13.0 |

It was found that most of the accumulated dirt could be removed at least just as well with the low-phosphorus or phosphorus-free detergents as with the phosphorus-containing reference products according to the state of the art. For stubborn, partly burnt dirt accumulations the detergents according to the invention were even superior to the reference products.

In a repetition of the tests described here, where hard tap water was used (16° dH), the findings obtained were the same as with the use of soft water; but an increase of the washing composition concentration to 5 gm/l was advisable.

EXAMPLE 2

For use with porcelain with delicate design, washing agents of the following composition are suitable.

| Component | % by weight of component in the product | | | | |
|---|---|---|---|---|---|
| | v | a | b | c | d |
| $Na_5P_3O_{10}$ | 61.0 | 47.0 | 22.0 | 10.0 | 0.0 |
| Aluminosilicate V | 0.0 | 21.0 | 42.0 | 52.0 | 61.0 |
| $Na_2SiO_3$ | 20.0 | 20.0 | 20.0 | 20.0 | 20.0 |
| $Na_2O \cdot 3.35\ SiO_2$ | 5.0 | 5.0 | 5.0 | 5.0 | 5.0 |
| $Na_2SO_4$ | 11.0 | 0.0 | 0.0 | 12.0 | 0.0 |
| DCIC | 2.0 | 2.0 | 2.0 | 2.0 | 2.0 |
| Non-ionic | 1.0 | 1.0 | 1.0 | 1.0 | 1.0 |
| Water | 0.0 | 4.0 | 8.0 | 8.0 | 11.0 |

EXAMPLE 3

For the production of granulates of the recipe indicated below suitable for use in household dishwashing machines, the non-ionic was dissolved in water, the liquid waterglass was added, and the solution was sprayed on a mixture of the remaining powdered, moving components, which was preferably done in granulating device, for example, on a granulating tray. After the water was bound as water of crystallization, the desired granulated material was obtained.

| Component | % by weight of component in the product | | | |
|---|---|---|---|---|
| | v | a | b | c |
| $Na_5P_3O_{10}$ | 45.0 | 20.0 | 5.0 | 0.0 |
| Aluminosilicate VII | 0.0 | 22.0 | 36.5 | 41.0 |
| $Na_2SiO_3$ | 32.2 | 32.2 | 32.2 | 32.2 |
| $Na_2CO_3$ | 6.5 | 6.5 | 6.5 | 6.5 |
| Liquid waterglass | 7.1 | 7.1 | 7.1 | 7.1 |
| DCIC | 2.0 | 2.0 | 2.0 | 2.0 |
| Non-ionic | 1.0 | 1.0 | 1.0 | 1.0 |
| Water | 6.2 | 9.2 | 9.7 | 10.2 |

The products are used in the same way as the products according to Examples 1 and 2. Quite similar results were obtained.

EXAMPLE 4

Compositions of the following components were found suitable for dishwashers in large kitchens, hotels, etc.

| Component | % by weight of component in the product | | | |
|---|---|---|---|---|
| | v | a | b | c |
| $Na_5P_3O_{10}$ | 51.0 | 25.0 | 11.0 | 0.0 |
| Aluminosilicate XII | 0.0 | 23.0 | 35.0 | 45.0 |
| $Na_2SiO_3$ | 10.0 | 10.0 | 10.0 | 10.0 |
| $Na_2SO_4$ | 16.0 | 16.0 | 16.0 | 16.0 |
| $Na_2CO_3$ | 22.0 | 22.0 | 22.0 | 22.0 |
| DCIC | 1.0 | 1.0 | 1.0 | 1.0 |
| $H_2O$ | 0.0 | 3.0 | 5.0 | 6.0 |

With a use at the rate of 2 to 4 gm/l, perfectly clean dishes were obtained.

EXAMPLE 5

The compositions of this example are suitable for the same purposes as those of Example 4. Because of their higher alkalinity, they are particularly suitable for use in commercial enterprises employing a very short action of the wash liquor, for example, only 10 to 20 seconds.

| Component | % by weight of component in the product | | | |
|---|---|---|---|---|
| | v | a | b | c |
| $Na_5P_3O_{10}$ | 47.0 | 22.0 | 7.0 | 0.0 |
| Aluminosilicate XII | 0.0 | 22.0 | 35.2 | 41.4 |
| $Na_2SiO_3$ | 12.0 | 12.0 | 12.0 | 12.0 |
| $Na_2CO_3$ | 25.0 | 25.0 | 25.0 | 25.0 |
| DCIC | 4.0 | 4.0 | 4.0 | 4.0 |
| NaOH | 12.0 | 12.0 | 12.0 | 12.0 |
| Water | 0.0 | 3.0 | 4.8 | 5.6 |

In the following examples, the compositions according to Examples 5, 10 and 20 are also suitable for laboratory dishwashers or for cleaning of wine, beer, milk, soft drink or mineral water bottles. When cleaning these bottles, it may be desirable to increase the content of sodium hydroxide in the detergents.

The following Examples 6 to 10 describe dishwasher washing agents which contain water-soluble salts of polymeric carboxylic acids in addition to aluminosilicates. The following substances can be used as sequestering polycarboxylic acids, preferably in the form of their sodium salts.

Polyacrylic acid
Poly-α-hydroxyacrylic acid
Polymaleic acid
Polyitaconic acid
Itaconic acid-aconitic acid copolymer
Itaconic acid-acrylic acid copolymer
Ethylene-maleic acid copolymer
Vinylmethyl ether-maleic acid copolymer
Isobutylene-maleic acid copolymer
Polyoxycarboxylic acid or POC 1 from acrolein and formaldehyde, P = 120, COOH: OH = 1.87
POC 2 from acrolein and formaldehyde, P = 3, COOH:OH = 4.0
POC 3 from acrolein, P = 50, COOH:OH = 8.6
POC 5 from acrolein and acrylic acid, P = 320, COOH:OH = 4.6
POC 6 from acrolein, acrylic acid and formaldehyde, P = 600, COOH:OH = 5.4
POC 7 from acrolein and formaldehyde, p = 5, COOH:OH = 1.5
POC 8 from acrolein and acrylic acid, P = 60, COOH:OH = 2.3
POC 9 from acrolein, acrylic acid and maleic acid, P = 65, COOH:OH = 4.9
POC 10 from acrolein, maleic acid and formaldehyde, P = 90, COOH:OH = 1.0
POC 11 from acrolein, acrylic acid and formaldehyde, P = 120, COOH:OH = 2.3
POC 12 from acrolein, P = 18, COOH:OH = 8.3

EXAMPLE 6

The test results described in Example 1 could also be obtained under the same test conditions (3 gm/l, 3° dH) with the following compositions:

| Component | % by weight of component in the product | | |
|---|---|---|---|
| | v | a | b |
| $Na_5P_3O_{10}$ | 44.0 | 20.0 | 0.0 |
| Aluminosilicate I | 0.0 | 15.0 | 26.0 |
| POC 1 | 0.0 | 9.0 | 18.0 |
| $Na_2SiO_3$ | 40.0 | 40.0 | 40.0 |
| $Na_2SO_4$ | 10.0 | 3.0 | 0.0 |
| DCIC | 2.0 | 2.0 | 2.0 |

-continued

| Component | % by weight of component in the product | | |
|---|---|---|---|
| | v | a | b |
| Non-ionic | 1.0 | 1.0 | 1.0 |
| Water | 3.0 | 10.0 | 13.0 |

In a repetition of the test described here, but using hard tap water (16° dH), the results obtained were the same as with the use of soft water.

EXAMPLE 7

Washing agents of the following composition are suitable for use for porcelain with delicate design

| Component | % by weight of component in the product | | | | |
|---|---|---|---|---|---|
| | v | a | b | c | d |
| $Na_5P_3O_{10}$ | 61.0 | 47.0 | 22.0 | 10.0 | 0.0 |
| Aluminosilicate V | 0.0 | 8.0 | 16.0 | 16.0 | 21.0 |
| POC 1 | 0.0 | 13.0 | 26.0 | 26.0 | 40.0 |
| $Na_2SiO_3$ | 20.0 | 20.0 | 20.0 | 20.0 | 20.0 |
| $Na_2O \cdot 3.35\ SiO_2$ | 5.0 | 5.0 | 5.0 | 5.0 | 5.0 |
| $Na_2SO_4$ | 11.0 | 0.0 | 0.0 | 12.0 | 0.0 |
| DCIC | 2.0 | 2.0 | 2.0 | 2.0 | 2.0 |
| Non-ionic | 1.0 | 1.0 | 1.0 | 1.0 | 1.0 |
| Water | 0.0 | 4.0 | 8.0 | 8.0 | 11.0 |

EXAMPLE 8

For the production of granulates of the formula indicated below for use in household dishwashing machines, the Non-ionic was dissolved in water, the liquid waterglass was added, and the solution was sprayed on a mixture of the remaining powdered, moving constituents, which was preferably done in a granulating device, for example, on a granulating tray. After the water was bound as water of crystallization, the desired granulated material was obtained.

| Component | % by weight of component in the product | | | |
|---|---|---|---|---|
| | v | a | b | c |
| $Na_5P_3O_{10}$ | 45.0 | 20.0 | 5.0 | 0.0 |
| Aluminosilicate VII | 0.0 | 14.0 | 22.5 | 25.0 |
| POC 1 | 0.0 | 8.0 | 14.0 | 16.0 |
| $Na_2SiO_3$ | 32.2 | 32.2 | 32.2 | 32.2 |
| $Na_2CO_3$ | 6.5 | 6.5 | 6.5 | 6.5 |
| Liquid waterglass | 7.1 | 7.1 | 7.1 | 7.1 |
| DCIC | 2.0 | 2.0 | 2.0 | 2.0 |
| Non-ionic | 1.0 | 1.0 | 1.0 | 1.0 |
| Water | 6.2 | 9.2 | 9.7 | 10.2 |

The products were used in the same way as the products according to Example 1 or 2 and 6 or 7 respectively. Quite similar results were obtained.

EXAMPLE 9

Agents of the following composition are suitable for use in dishwashing machines of large kitchens, hotels, etc.

| Component | % by weight of component in the product | | | |
|---|---|---|---|---|
| | v | a | b | c |
| $Na_5P_3O_{10}$ | 51.0 | 25.0 | 11.0 | 0.0 |
| Aluminosilicate | 0.0 | 15.0 | 20.0 | 30.0 |
| POC 1 | 0.0 | 8.0 | 15.0 | 15.0 |
| $Na_2SiO_3$ | 10.0 | 10.0 | 10.0 | 10.0 |
| $Na_2SO_4$ | 16.0 | 16.0 | 16.0 | 16.0 |
| $Na_2CO_3$ | 22.0 | 22.0 | 22.0 | 22.0 |
| DCIC | 1.0 | 1.0 | 1.0 | 1.0 |
| $H_2O$ | 0.0 | 3.0 | 5.0 | 6.0 |

With a dose of 2 to 4 gm/l, perfectly clean dishes were obtained.

EXAMPLE 10

The cleaning agents of this example are suitable for the same purposes as those of Example 4. Because of their higher alkalinity they are particularly suitable for use in commercial machines with very short duration of action of the liquor, for example 10 to 20 seconds.

| Component | % by weight of component in the product | | | |
|---|---|---|---|---|
| | v | a | b | c |
| $Na_5P_3O_{10}$ | 47.0 | 22.0 | 7.0 | 0.0 |
| Aluminosilicate XII | 0.0 | 11.0 | 17.6 | 20.7 |
| POC 1 | 0.0 | 11.0 | 17.0 | 20.7 |
| $Na_2SiO_3$ | 12.0 | 12.0 | 12.0 | 12.0 |
| $Na_2CO_3$ | 25.0 | 25.0 | 25.0 | 25.0 |
| DCIC | 4.0 | 4.0 | 4.0 | 4.0 |
| NaOH | 12.0 | 12.0 | 12.0 | 12.0 |
| Water | 0.0 | 3.0 | 4.8 | 5.6 |

The following Examples 11 to 15 describe compositions according to the invention where the aluminosilicates were partly replaced by a water-insoluble ion-exchange resin. (Here too water-soluble salts of polymeric carboxylic acids can be used additionally). A resin of a crosslinked polystyrene-sulfonic acid basis with a calcium binding power of 135 mg CaO/gm active substance and a particle size of 0.3 to 0.8 mm (commercial product: "Lewatit S 100") was employed as an ion-exchange resin.

EXAMPLE 11

The test results described in Example 1 could also be obtained under the same test conditions (3 gm/l, 3° dH) with the following compositions:

| Component | % by weight of component in the product | | |
|---|---|---|---|
| | v | a | b |
| $Na_5P_3O_{10}$ | 44.0 | 20.0 | 0.0 |
| Aluminosilicate I | 0.0 | 15.0 | 26.0 |
| Ion-exchange resin | 0.0 | 9.0 | 18.0 |
| $Na_2SiO_3$ | 40.0 | 40.0 | 40.0 |
| $Na_2SO_4$ | 10.0 | 3.0 | 0.0 |
| DCIC | 2.0 | 2.0 | 2.0 |
| Non-ionic | 1.0 | 1.0 | 1.0 |
| Water | 3.0 | 10.0 | 13.0 |

In a repetition of the tests described here, but using hard tap water (16° dH), the same results were obtained as with the use of soft water.

EXAMPLE 12

Agents of the following composition are suitable for use for percelain with delicate design.

| Component | % by weight of component in the product | | | | |
|---|---|---|---|---|---|
| | v | a | b | c | d |
| $Na_5P_3O_{10}$ | 61.0 | 47.0 | 22.0 | 10.0 | 0.0 |
| Aluminosilicate V | 0.0 | 8.0 | 16.0 | 16.0 | 21.0 |
| Ion exchange resin | 0.0 | 13.0 | 26.0 | 26.0 | 40.0 |
| $Na_2SiO_3$ | 20.0 | 20.0 | 20.0 | 20.0 | 20.0 |
| $Na_2O \cdot 3.35\ SiO_2$ | 5.0 | 5.0 | 5.0 | 5.0 | 5.0 |
| $Na_2SO_4$ | 11.0 | 0.0 | 0.0 | 12.0 | 0.0 |
| DCIC | 2.0 | 2.0 | 2.0 | 2.0 | 2.0 |
| Non-ionic | 1.0 | 1.0 | 1.0 | 1.0 | 1.0 |
| Water | 0.0 | 4.0 | 8.0 | 8.0 | 11.0 |

EXAMPLE 13

For the production of granulates of the formula indicated below for use in household dishwashing machines, the Non-ionic was dissolved in water, the liquid waterglass was added, and the solution was sprayed on a mixture of the remaining powdered, moving components, which was done preferably in a granulating device, for example, on a granulating tray. After the water was bound as water of crystallization, the desired granulated material was obtained.

| Component | % by weight of component in the product | | | |
|---|---|---|---|---|
| | v | a | b | c |
| $Na_5P_3O_{10}$ | 45.0 | 20.0 | 5.0 | 0.0 |
| Aluminosilicate VII | 0.0 | 14.0 | 22.5 | 25.0 |
| Ion exchange resin | 0.0 | 8.0 | 14.0 | 16.0 |
| $Na_2SiO_3$ | 32.2 | 32.2 | 32.2 | 32.2 |
| $Na_2SiO_3$ | 6.5 | 6.5 | 6.5 | 6.5 |
| Liquid waterglass | 7.1 | 7.1 | 7.1 | 7.1 |
| DCIC | 2.0 | 2.0 | 2.0 | 2.0 |
| Non-ionic | 1.0 | 1.0 | 1.0 | 1.0 |
| Water | 6.2 | 9.2 | 9.7 | 10.2 |

The products were used in the same way as the products according to Example 1 or 2 and 11 or 12 respectively. The results obtained were quite similar.

EXAMPLE 14

Agents of the following composition are suitable for use in dishwashing machines of large kitchens, hotels, etc.

| Component | % by weight of component in the product | | | |
|---|---|---|---|---|
| | v | a | b | c |
| $Na_5P_3O_{10}$ | 51.0 | 25.0 | 11.0 | 0.0 |
| Aluminosilicate XII | 0.0 | 15.0 | 20.0 | 30.0 |
| Ion exchange resin | 0.0 | 8.0 | 15.0 | 15.0 |
| $Na_2SiO_3$ | 10.0 | 10.0 | 10.0 | 10.0 |
| $Na_2SO_4$ | 16.0 | 16.0 | 16.0 | 16.0 |
| $Na_2CO_3$ | 22.0 | 22.0 | 22.0 | 22.0 |
| DCIC | 1.0 | 1.0 | 1.0 | 1.0 |
| Water | 0.0 | 3.0 | 5.0 | 6.0 |

With a dose of 2 to 4 gm/l, perfectly clean dishes were obtained.

EXAMPLE 15

The cleaners of this example are particularly suitable for the same purposes as those of Examples 4 and 14. Because of their higher alkalinity, they are particularly suitable for use in commercial machines with a very short action of the liquor, for example only 10 to 20 second.

| Component | % by weight of component in the product | | | |
|---|---|---|---|---|
| | v | a | b | c |
| $Na_5P_3O_{10}$ | 47.0 | 22.0 | 7.0 | 0.0 |
| Aluminosilicate XII | 0.0 | 11.0 | 17.6 | 20.7 |
| Ion exchange resin | 0.0 | 11.0 | 17.0 | 20.7 |
| $Na_2SiO_3$ | 12.0 | 12.0 | 12.0 | 12.0 |
| $Na_2CO_3$ | 25.0 | 25.0 | 25.0 | 25.0 |
| DCIC | 4.0 | 4.0 | 4.0 | 4.0 |
| NaOH | 12.0 | 12.0 | 12.0 | 12.0 |
| Water | 0.0 | 3.0 | 4.8 | 5.6 |

When the action of the products according to the invention are compared with corresponding products containing tripolyphosphate, but no aluminosilicate, the beneficial action of the products according to the invention are apparent. The normal dirt accumulations in practice were dissolved at least just as well with the washing agents according to the invention as with the reference products. In very stubborn cases, the products according to the invention were frequently even superior to the reference products.

A deposit of the water-insoluble aluminosilicates in the liquor tanks of large dishwashing machines was not found, at least not when the liquor was kept constantly in motion and the aluminosilicate was circulated. In order to positively avoid irreversible deposits of aluminosilicates during standstills, it is advisable to install suitable devices in the liquor tanks which permit agitation of the liquor containing aluminosilicates or to impart to the bottom of the liquor tank an inclination so that any deposited particles slide down to the lowest point where they are returned into the liquor circuit by the suction pipe of the liquor pump.

In this respect the microcrystalline aluminosilicates proved particularly advantageous. This was found when the aluminosilicates used in Examples 1 to 5 were replaced by microcrystalline products. These were the following aluminosilicates.

Im: $0.9\ Na_2O \cdot Al_2O_3 \cdot 2.04\ SiO_2 \cdot 4.3\ H_2O$ (=21.6% $H_2O$) Fully crystalline Calcium binding power: 170 mg CaO/gm AS XIIm: $0.9\ Na_2O \cdot Al_2O_3 \cdot 2\ SiO_2 \cdot 3\ H_2O$ (=11% $H_2O$) Fully crystalline Calcium binding power: 175 mg CaO/gm AS XIIIM: $0.28\ Na_2O \cdot 0.62\ K_2O \cdot Al_2O_3 \cdot 2.04\ SiO_2 \cdot 4.3\ H_2O$ (=20.5% $H_2O$) Fully crystalline Calcium binding power: 150 mg CaO/gm AS XVIIIM: $0.9\ Na_2O \cdot Al_2O_3 \cdot 2\ SiO_2 \cdot 4.4\ H_2O$ (=22.2% $H_2O$) Fully crystalline Calcium binding power: 172 mg CaO/gm AS The following examples describe products which contain microcrystalline aluminosilicates.

EXAMPLE 16

The test results described in Example 1 could also be obtained under the same conditions (3 gm/l; 3° dH) with agents of the following composition:

| Component | % by weight of component in the product | | |
|---|---|---|---|
| | v | a | b |
| $Na_5P_3O_{10}$ | 44.0 | 20.0 | 0.0 |
| Aluminosilicate Im | 0.0 | 24.0 | 44.0 |
| $Na_2SiO_3$ | 40.0 | 40.0 | 40.0 |
| $Na_2SO_4$ | 10.0 | 3.0 | 0.0 |
| Non-ionic | 1.0 | 1.0 | 1.0 |
| DCIC | 2.0 | 2.0 | 2.0 |
| Water | 3.0 | 10.0 | 13.0 |

EXAMPLE 17

Agents of the following composition are suitable for use for porcelain with delicate design:

| Component | % by weight of component in the product | | | | |
|---|---|---|---|---|---|
| | v | a | b | c | d |
| $Na_5P_3O_{10}$ | 61.0 | 47.0 | 22.0 | 10.0 | 0.0 |
| Aluminosilicate XVIIIm | 0.0 | 19.5 | 39.0 | 39.0 | 56.0 |
| $Na_2SiO_3$ | 20.0 | 20.0 | 20.0 | 20.0 | 20.0 |
| $Na_2O \cdot 3.35\ SiO_2$ | 5.0 | 5.0 | 5.0 | 5.0 | 5.0 |
| $Na_2SO_4$ | 11.0 | 0.0 | 0.0 | 12.0 | 0.0 |
| DCIC | 2.0 | 2.0 | 2.0 | 2.0 | 2.0 |
| Non-ionic | 1.0 | 1.0 | 1.0 | 1.0 | 1.0 |
| Water | 0.0 | 5.5 | 11.0 | 11.0 | 16.0 |

EXAMPLE 18

For the production of granulates of the formula indicated below for use in household dishwashing machines, the Non-ionic was dissolved in water, the liquid waterglass was added, and the solution was sprayed on a mixture of the remaining powdered, moving components, which was preferably done in a granulating device, for example, on a granulating tray. After the water was bound as water of crystallization, the desired granulate material was obtained.

| Component | % by weight of component in the product | | | |
|---|---|---|---|---|
| | v | a | b | c |
| $Na_5P_3O_{10}$ | 45.0 | 20.0 | 5.0 | 0.0 |
| Aluminosilicate XIIIm | 0.0 | 20.0 | 32.0 | 36.0 |
| $Na_2SiO_3$ | 32.2 | 32.2 | 32.2 | 32.2 |
| $Na_2CO_3$ | 6.5 | 6.5 | 6.5 | 6.5 |
| Liquid Waterglass | 7.1 | 7.1 | 7.1 | 7.1 |
| DCIC | 2.0 | 2.0 | 2.0 | 2.0 |
| Non-ionic | 1.0 | 1.0 | 1.0 | 1.0 |
| Water | 6.2 | 11.2 | 14.2 | 15.2 |

These products can be employed in equal respects as the products according to Examples 1 and 2 or 16 and 17 respectively. Similar results were obtained thereby.

EXAMPLE 19

An agent of the following composition can be employed for use in commercial dishwashers in large kitchens, hotels, etc.

| Component | % by weight of component in the product | | | |
|---|---|---|---|---|
| | v | a | b | c |
| $Na_5P_3O_{10}$ | 51.0 | 25.0 | 11.0 | 0.0 |
| Aluminosilicate XIIm | 0.0 | 23.0 | 35.0 | 45.0 |
| $Na_2SiO_3$ | 10.0 | 10.0 | 10.0 | 10.0 |
| $Na_2SO_4$ | 16.0 | 16.0 | 16.0 | 16.0 |
| $Na_2CO_3$ | 22.0 | 22.0 | 22.0 | 22.0 |
| DCIC | 1.0 | 1.0 | 1.0 | 1.0 |
| $H_2O$ | 0.0 | 3.0 | 5.0 | 6.0 |

At a level of from 2 to 4 gm/1, unobjectionably clean dishes were obtained.

EXAMPLE 20

The cleaners of this example are suitable for the same purposes as those of Example 4. Because of their higher alkalinity they are particularly suitable for use in commercial machines with a very short action of the liquor, for example only 10 to 20 seconds.

| Component | % by weight of component in the product | | | |
|---|---|---|---|---|
| | v | a | b | c |
| $Na_5P_3O_{10}$ | 47.0 | 22.0 | 7.0 | 0.0 |
| Aluminosilicate XIIm | 0.0 | 22.0 | 35.2 | 41.4 |
| $Na_2SiO_3$ | 12.0 | 12.0 | 12.0 | 12.0 |
| $Na_2CO_3$ | 25.0 | 25.0 | 25.0 | 25.0 |
| DCIC | 4.0 | 4.0 | 4.0 | 4.0 |
| NaOH | 12.0 | 12.0 | 12.0 | 12.0 |
| Water | 0.0 | 3.0 | 4.8 | 5.6 |

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. In the process of mechanically washing of soiled dishes by mechanically contacting soiled dishes with an alkaline aqueous solution at a pH of from 8 to 13 containing a sufficient amount of a water softening agent whereby the soil on said soiled dishes is dispersed or dissolved, rinsing said dishes with a clear rinse liquid and recovering said dishes substantially soil-free, the improvement which consists of using a composition for use in mechanical dishwashers consisting essentially of (A) 44 percent by weight on the anhydrous basis of a finely-dispersed water-insoluble aluminosilicate compound having primary particles in the size range of 100 $\mu$ to 0.1 $\mu$, a calcium binding power of 150 mg CaO/gm of anhydrous substance when measured at 22° C by the Calcium Binding Power Test Method described in the specification and the formula $$, 0.9\ Na_2O \cdot Al_2O_3 \cdot 2.05\ SiO_2 \cdot 4.3\ H_2O$$

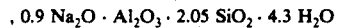

(B) 40 percent by weight of $Na_2SiO_3$, (C) 2 percent by weight of the sodium or potassium salt of dichloroisocyanuric acid, (D) 1 percent by weight of a nonionic block polymer of ethylene oxide to polyoxypropylene glycol with a molecular weight of 1900 where the amount of polyethylene glycol ethers is 10% by weight and (E) 13 percent by weight of water, as said water softening agent, in such an amount that said alkaline aqueous solution contains from 3 to 5 gm per liter of said composition.

* * * * *